United States Patent [19]

Davenport et al.

[11] Patent Number: 4,994,623

[45] Date of Patent: Feb. 19, 1991

[54] PROCESS FOR PRODUCING THIOALKYL OR THIOARYLPHENONES

[75] Inventors: Kenneth G. Davenport, Hofheim, Fed. Rep. of Germany; Wilson B. Ray, Beeville; Mohammad Aslam, Corpus Christi, both of Tex.

[73] Assignee: Hoechst Celanese Corporation, Somerville, N.J.

[21] Appl. No.: 500,112

[22] Filed: Mar. 27, 1990

Related U.S. Application Data

[63] Continuation of Ser. No. 247,985, Sep. 21, 1988, abandoned.

[51] Int. Cl.$^5$ .......................................... C07C 319/12
[52] U.S. Cl. ...................................................... 568/42
[58] Field of Search .......................................... 568/42

[56] References Cited

U.S. PATENT DOCUMENTS

| | | | |
|---|---|---|---|
| 2,833,825 | 5/1958 | Lewis | 260/592 |
| 4,082,807 | 4/1978 | Eiglmeier | 260/590 R |
| 4,453,012 | 6/1984 | Desbois | 568/323 |
| 4,474,990 | 10/1984 | Jansons | 568/319 |
| 4,560,789 | 12/1985 | Davenport et al. | 560/142 |
| 4,568,763 | 2/1986 | Davenport et al. | 560/142 |
| 4,593,125 | 6/1986 | Davenport et al. | 568/323 |
| 4,607,125 | 8/1986 | Mott | 568/323 |
| 4,618,726 | 10/1986 | Desbois | 568/42 |
| 4,670,603 | 6/1987 | Piccolo et al. | 568/319 |
| 4,894,482 | 1/1990 | Lindley et al. | 568/42 |

FOREIGN PATENT DOCUMENTS 2616986  10/1977  Fed. Rep. of Germany ........ 568/42

OTHER PUBLICATIONS

"New Photoinitiators for Pigmented Systems", *Technical Paper*, FC 84–989, Society of Manufacturing Engineers, 1984, pp. 1–22.

Dann and Mylius, Annalen der Chemie, 587, Band, 1–15, W. Germany, 1954.

"Hydrogen Fluoride as a Condensing Agent. VII. The Acylation of Aromatic Compounds", *Journal of the American Chemical Society*, vol. 1, 61, Jul. 1939.

Modern Synthetic Reactions, Herbert O. House, W. A. Benjamin, Inc., Publishers, 1972, p. 9.

Advanced Organic Chemistry, Second Edition, Jerry March, McGraww-Hill Book Co., pp. 466 and 1104.

*Primary Examiner*—James H. Reamer
*Attorney, Agent, or Firm*—Shirley L. Church

[57] ABSTRACT

Thiophenones are produced by acylating the aromatic ring of thiophenolic ethers in the presence of anhydrous hydrofluoric acid. It has been found that if the thio group is in the form of a thioether and not a thiol, the aromatic ring can be acylated to form the thiophenone in the presence of anhydrous hydrofluoric acid.

10 Claims, No Drawings

PROCESS FOR PRODUCING THIOALKYL OR THIOARYLPHENONES

This application is a continuation of application Ser. No. 247,985, filed 9/21/88 now abandoned.

FIELD OF THE INVENTION

The present invention is directed to a process for synthesizing thiophenones by acylating the aromatic ring of thiophenolic ethers in the presence of hydrofluoric acid.

BACKGROUND OF THE INVENTION

Thioalkyl- and thioarylphenones have importance as chemical intermediates inasmuch as such compounds can be derivatized at the thio group or the carbonyl group. Such compounds have use as intermediates in the production of agricultural and pharmaceutical chemicals among other chemical uses. One particular thioaromatic ketone which has been synthesized is 4'-thiomethylisobutylphenone. This compound is used as an intermediate for a UV-cure photoinitiator, IRGACURE 907 (manufactured by Ciba Geigy). The disclosed process for forming this particular thioalkylphenone involves the reaction of thioanisole with acetyl halide in the presence of an aluminum chloride catalyst. Unfortunately, aluminum chloride is not a recyclable catalyst and upon termination of reaction must be disposed of as waste. Furthermore, the use of acetyl chloride with subsequent hydrogen chloride evolution and solids handling add to the cost of production.

It is known to produce hydroxy aromatic ketones by reacting a phenol in liquid anhydrous hydrofluoric acid with a carboxyl halide to acylate the phenolic ring. German Offenlegungsschrift 2,616,986 discloses such a reaction wherein examples of aliphatic and aromatic carboxyl halides include acetyl chloride, propionyl chloride, caprylyl fluoride, benzoyl chloride, oxalyl chloride, succinyl chloride, 3-chlorobenzyl chloride, β-phenylpropionyl chloride and examples of suitable phenol components include phenol, hydroquinone, pyrocatechol, resorcinol, m-, o- and p-chlorophenol, m-, o- and p-cresol, m-nitrophenol, guaiacol, m-methoxyphenol, 7-chloro-2-naphthol, β-naphthol, and 4-methyl resorcinol.

The same type of reaction is disclosed in U.S. Pat. Nos. 4,560,789 and 4,568,763 in which phenol is reacted with acetic acid in HF to form 4-hydroxyacetophenone.

U.S. Pat. No. 2,833,825 discloses the isomerization of a phenol ester by means of liquid HF to give the acylphenol. A similar reaction is disclosed in Dann and Mylius, Annalen der Chemie, 587, Band, 1-15, W. Germany, 1954. The use of HF to acylate aromatic rings with acid reactants is disclosed in the *Journal of the American Chemical Society*, Vol. 61, July 1939 in an article entitled "Hydrogen Fluoride as a Condensing Agent. The Acylation of Aromatic Compounds", Simons et al.

There has been no suggestion in the art, including that described above, of acylating ring atoms of thiophenolic ethers with acylating agents in the presence of HF to form thiophenones. An important feature of HF is that the catalyst can be recycled and reused and, thus, would have an advantage over the nonrecyclable aluminum chloride as acylation catalyst. Furthermore, the evolution of hydrogen chloride and solids handling can be eliminated by use of acylating agents other than carboxylic acid halides in the presence of HF.

SUMMARY OF THE INVENTION

It has now been found that the ring of thiophenolic ethers can be acylated in liquid HF to form thioalkyl- or thioarylphenones The reaction can be characterized as follows:

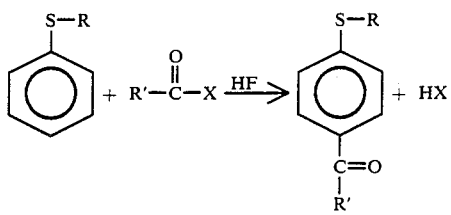

wherein R and R' are alkyl or aryl; X is a halide or OR"; and R" is hydrogen or a

group to yield a carboxylic acid or anhydride.

In order for the ring of the thiophenolic compound to be acylated, it is important that the thio group be in the form of a thioether. Thus, the reaction of thiophenol with an acylating agent in the presence of HF does not result in acylation of the aromatic ring but reaction with the thiol group as well as dimerization of the thiol to afford diaryl disulfides and acylated diaryldisulfides.

DETAILED DESCRIPTION OF THE INVENTION

The present invention concerns a process for producing thioalkyl- or thioarylphenone of the general formula:

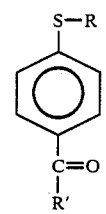

wherein R and R' stand for an alkyl group containing, for example, from 1 to 12 carbon atoms, or an aryl group, or substituted alkyl or aryl groups.

The thiophenone is produced by treating a thiophenolic ether of the formula:

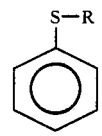

wherein R is as defined above, in anhydrous hydrofluoric acid with a carboxylic acid, halide or anhydride of the formula:

wherein R' is as defined above; X is a halide selected from F, Cl, Br and I or X stands for OR", wherein R" is hydrogen or equivalent to a

group to provide a carboxylic acid or an acid anhydride as the acylating agent.

It has been found that thiophenones, especially p-thiophenones, can be produced in excellent yield and with a high purity if the thiophenolic ethers are treated directly with the corresponding carboxylic acid, halide or anhydride in liquid HF. On the other hand, it has been found that the thiophenol compound will not undergo acylation at the ring, but at the thiol group. It has been observed in anhydrous hydrofluoric acid thiophenolic compounds also undergo oxidation to afford diaryldisulfides and acylated diaryldisulfides. Thus, the thiophenolic compound to be acylated at the ring must be in the form of a thiophenolic ether and not as a thiol.

The reaction according to this invention is carried out in anhydrous liquid hydrofluoric acid. The hydrofluoric acid may be of technical grade but should not contain more than about 5 wt. % water. Although a solvent is not necessary for the reaction, a known Friedel-Crafts reaction solvent can be used including $CH_2Cl_2$, $C_2H_4Cl_2$, $C_2H_2Cl_4$, etc.

The process according to this invention may be carried out at temperatures between about room temperature to 120° C., preferably between about 40° and 70° C. The reaction time is generally between about 30 minutes and 4 hours. The reaction can be carried at atmospheric pressure and, if necessary, also at elevated pressure, up to about 150 psig.

The mol ratio of HF to thiophenolic ether should be between about 1 and 100. It is preferred to provide a molar excess of carboxylic acid, halide or anhydride acylating agent relative to the amount of thiophenolic ether present. Thus for every mole of thiophenolic ether, there should be present 1 to 2 moles of acylating agent.

The thiophenolic ether and acylating agent can be mixed together in the reactor prior to addition of HF or the acylating agent may be added subsequent to the addition of hydrofluoric acid to the thiophenolic ether. Upon addition of the HF, the reaction pressure increases. At this time the reactants are brought to reaction temperature which is maintained to completion of the reaction. The resulting thiophenone can be separated by distillative separation of the HF from the reaction products and solvent extraction of the product from an aqueous phase The HF can thus be recovered and recycled to the process.

The process according to this invention including reaction and recovery of the produce is illustrated in greater detail in the following examples. Unless otherwise indicated, all percentage amounts are weight percent.

EXAMPLE 1

Thioanisole (12.4 g, 0.10 mol) and acetic anhydride (15.3 g, 0.15 mol) were charged to a 300 mL Hastelloy C autoclave at room temperature and the reactor sealed. The reactor was checked for leaks at 50 psig nitrogen, the nitrogen evacuated from the reactor and the reactor cooled to −40° C. to yield a reactor pressure of 50 mm Hg. Hydrogen fluoride (80 g, 4 mol) was transferred into the reactor and the reactor was heated to 50° C. and maintained for 2 hours. Upon conclusion of the reaction, the reactor was cooled to 20° C. and the excess HF was vented to a KOH scrubber. The product was dissolved in ethyl acetate and neutralized with 45% aqueous potassium hydroxide. The resulting organic phase was separated, dried over $MgSO_4$ and the organic phase concentrated at reduced pressure to yield 16.6 grams of a yellow solid. GC analysis indicated that 98.2% of the product was 4'-thiomethylacetophenone and 0.7% was the 2-isomer thereof.

EXAMPLE 2

Thioanisole (12.4 g, 0.10 mol) was treated with isobutyric anhydride (23.7 g, 0.15 mol) in the presence of HF (80 g, 4 mol) by the procedure as described in Example 1. The crude product was isolated as in Example 1 to afford 29.7 grams of a black liquid. Distillation of isobutyric acid at reduced pressure yielded 13.6 grams of an off-white wet crystalline material. Analysis by GC indicated 63 wt. % of 4'-thiomethylisobutylphenone. Upon recrystallation of 9 grams of the residue from ethanol, the product was found to contain 93 wt. % of 4'-thiomethylisobutylphenone.

EXAMPLE 3

Thiophenol (11.0 g, 0.10 mol) and acetic anhydride (15.3 g, 0.15 mol) were added to a Hastelloy C reactor as in Example 1. The reactor was checked for leaks with nitrogen, the nitrogen evacuated and the reactor cooled to −20° C. and 50 mm Hg. Hydrogen fluoride (80 g, 4 mol) was transferred into the reactor. The reactor was heated and the reaction temperature was maintained at about 70° C. for 3 hours.

Upon completion of the reaction, the product was isolated by removal of HF and extraction with ethyl acetate as described in Example 1 to yield 11.3 g of a green solid. Analysis of the product by GC and GC/MS did not show any formation of 4'-thiolacetophenone.

What is claimed is:

1. A process for synthesizing thiophenones by reacting a thiophenolic ether of the formula:

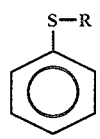

wherein R is as an alkyl group containing from 1 to 12 carbon atoms or an aryl group with an acylating agent of the formula:

wherein R' is an alkyl group containing from 1 to 12 carbon atoms or an aryl group;
and X is a halide or OR", wherein R" is hydrogen or a

group to provide a carboxylic acid or anhydride as the acylating agent to acylate and para-position of said thiophenolic ether at a selectivity of greater than 90% to yield a thiophenone of the formula:

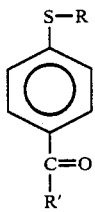

wherein R and R' are as defined above.

2. The process of claim 1 wherein said reaction temperature ranges from about 40° to about 70° C.

3. The process of claim 1 wherein said reaction pressure ranges from about atmospheric pressure to about 150 psig.

4. The process of claim 1 wherein the mol ratio of HF to thiophenolic ether is from about 1 to 100.

5. The process of claim 1 wherein there is a molar excess of said acylating agent relative to said thiophenolic ether.

6. The process of claim 1 wherein said acylating agent is an acid anhydride.

7. The process of claim 1 wherein X is a halide selected from F, Cl, Br and I.

8. The process of claim 1 wherein said acylating agent is a carboxylic acid.

9. The process of claim 1 wherein said thiopenolic ether is thioanisole.

10. The process of claim 6 wherein said acylating agent is acetic or isobutyric anhydride.

* * * * *